US00PP08127P

United States Patent [19]

Man

[11] Patent Number: Plant 8,127

[45] Date of Patent: Feb. 2, 1993

[54] POINSETTIA PLANT 'GOLDFINGER'

[76] Inventor: Jan Man, Meerlandenweg 46, 1187 ZR Amstelveen, Netherlands

[21] Appl. No.: 745,217

[22] Filed: Aug. 14, 1991

[51] Int. Cl.[5] ..... A01H 5/00

[52] U.S. Cl. ..... Plt./86.4

[58] Field of Search ..... Plt./86.3, 86.4

[56] References Cited

U.S. PATENT DOCUMENTS

P.P. 5,492 6/1985 Gutbier ..... Plt. 86.3

P.P. 7,310 8/1990 Neuhaus ..... Plt. 86.3

*Primary Examiner*—James R. Feyrer

*Attorney, Agent, or Firm*—Arnold, White & Durkee

[57] ABSTRACT

The present invention describes a Poinsettia cultivar, designated 'Goldfinger', that is vigorous and self-branching, having a medium to tall height with bright red flower bracts. 'Goldfinger' originated as a seedling from the cross pollination of cultivar 15-84 (U.S. Plant Pat. No. 7,310) and cultivar 'Angelika' (U.S. Plant No. 5,492). 'Goldfinger' is more vigorous, and blooms earlier than 'Angelika', the cultivar it most closely resembles. 'Goldfinger' has fewer bracts than 'Angelika', and they are smoother than those of 'Angelika'. The cyathia retention is longer for 'Goldfinger' than 'Angelika'.

1 Drawing Sheet

BACKGROUND OF THE INVENTION

'Goldfinger' is a vigorous, strong growing Poinsettia of medium to tall height and large, bright red flower bracts. It has self-branching traits which make it desirable for branched plant production. 'Goldfinger' blooms relatively early and the blooming time is very uniform among individual clones. The bracts develop in a horizontal plane and do not hang downwards after sleeving and shipping. The cyathia do not prematurely abscise.

This new Poinsettia cultivar originated as a seedling from cross pollination of '15-84' (U.S. Plant Pat. No. 7,310) and 'Angelika' (U.S. Plant Pat. No. 5,492) in our greenhouses in Aalsmeer, Holland. It most closely resembles the cultivar 'Angelika' of U.S. Plant Pat. No. 5,492 but distinctly differs in the following traits. 'Goldfinger' grows taller and is more vigorouos than 'Angelika'. The number of uniformly colored bracts are fewer than 'Angelika'. The bract surface is relatively smoother than 'Angelika'. There is red coloration of the nectar cup on 'Goldfinger' but not on the nectar cup of 'Angelika'. 'Goldfinger' blooms 3–4 days earlier than 'Angelika' and the cyathia persist longer.

After selection, vegetative reproduction of this plant was accomplished by stem cuttings for further testing purposes. Clones were subjected to successive generations of vegetative propagation which demonstrated that bract coloration and other distinctive characteristics held true from generation to generation.

DESCRIPTION OF THE PHOTOGRAPHS

Poinsettia cultivar 'Goldfinger' is illustrated in the accompanying color photographs.

The upper photo is a side view of a typical pinched plant with several flowering stems.

The lower photo is a top view of five single stemmed plants in one pot, showing flower and bract formation.

DESCRIPTION OF THE PLANT

The following is a detailed description of this new Poinsettia as observed in our greenhouses in Aalsmeer, Holland, during December, 1990. Some observations are compared to the cultivar 'Angelika', U.S. Plant Pat. No. 5,492, grown at the same time, in the same greenhouse under the same cultural conditions at the Research Centre for Horticulture, Aarslev, Denmark. Color designations were compared to the 1986 edition of R.H.S. Colour Chart, first published in 1966 by The Royal Horticultural Society, London, England.

THE PLANT

Origin: Seedling from cross pollination.

Classification:

*Botanic.*—*Euphorbia pulcherrima* Willd.

*Common name.*—Poinsettia.

*Cultivar name.*—'Goldfinger'.

Form: Shrub.

Height: Medium to tall.

Growth habit: As a single stemmed plant, upright and vigorous. In full flower, the stem is terminated by a large inflorescence, with smaller flowering side shoots lower on the stem. The average overall height of single stemmed plants was 48 cm. for the invention, compared to 40 cm. height for 'Angelika'.

Branching: Branching can be enhanced by removal of the stem tip. Then, several flowering branches with equal vigor will develop on a single plant.

Growth rate: Very fast. Rooting of stem cuttings occurs in 12–18 days under intermittent mist. The plant will flower in about nine weeks under continuous long night conditions and night temperatures of about 16–18 degrees C. Flowering is 3–4 days earlier than 'Angelika'.

Foliage: The foliage is clean and uniformly green from bottom to top of the plant. The leaves are of medium size, leaf blades typically being 14–16 cm. long and about 8–9 cm. wide with leaf petioles 6–7 cm. long.

Leaf shape.—Typical leaves are ovate with obtuse bases and acuminate tips. Leaf margins are entire to modestly lobed with usually one lobe on either side of the leaf blade.

Leaf surface.—Upper surface is glabrous and slightly rugose. The under surface is slightly pubescent.

*Leaf color.*—Upper side — Between RHS 147A and RHS 147B. Under side — Near RHS 137C.

*Retention.*—The foliage retention is good even under low light intensities in the consumer's home.

Bracts: Generally there are about 16 bracts of various sizes subtending the cyathia. The primary bracts have blades typically 14–16 cm. long and about 10 cm. wide with petioles 2–3 cm. long. The bracts are fewer in number than for 'Angelika', which typically has about 20 fully colored bracts of various sizes.

*Shape.*—Bracts are mostly ovate with acute bases and acuminate tips. Bract margins are mostly entire, but primary bracts may have slight lobing on either side of the bracts.

*Surface.*—The bract surface is only slightly rugose and smoother than the bract surface of 'Angelika'.

*Color.*—Upper side — Bright red. Darker than RHS 46C, near RHS 46B. The color of the margins is lighter compared to the main part. Under side — Red, near RHS 47A.

Cyathia: Generally, 12–15 cyathia (flowers) develop when the plant is in "full bloom." Each cyathium is 6–7 mm long and 5–6 mm wide, green in color and fringed with red at the distal end. Usually, two yellow nectar cups tinged with red protrude from the side of each cyathium. Red coloration of the nectar cups is absent in 'Angelika'. The flower pedicel is green and 5–6 mm in length. The stamens protruding from the cyathia are red.

*Retention.*—The post-production retention of the cyathia is good, and their persistence is 6 days longer than 'Angelika'.

What is claimed is:

1. A new and distinct Poinsettia cultivar, substantially as herein shown and described, distinguished by its vigorous and self-branching growth habits, medium to tall height and bright red flower bracts.

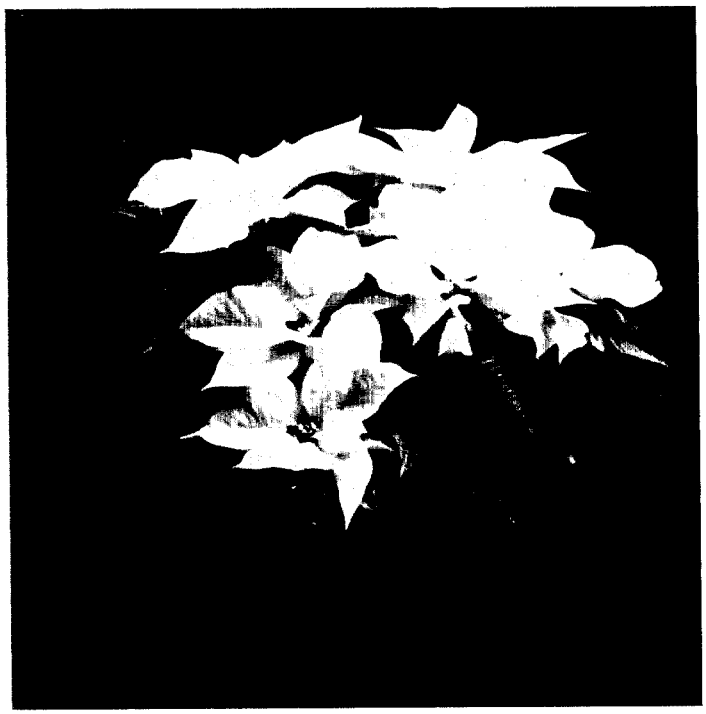
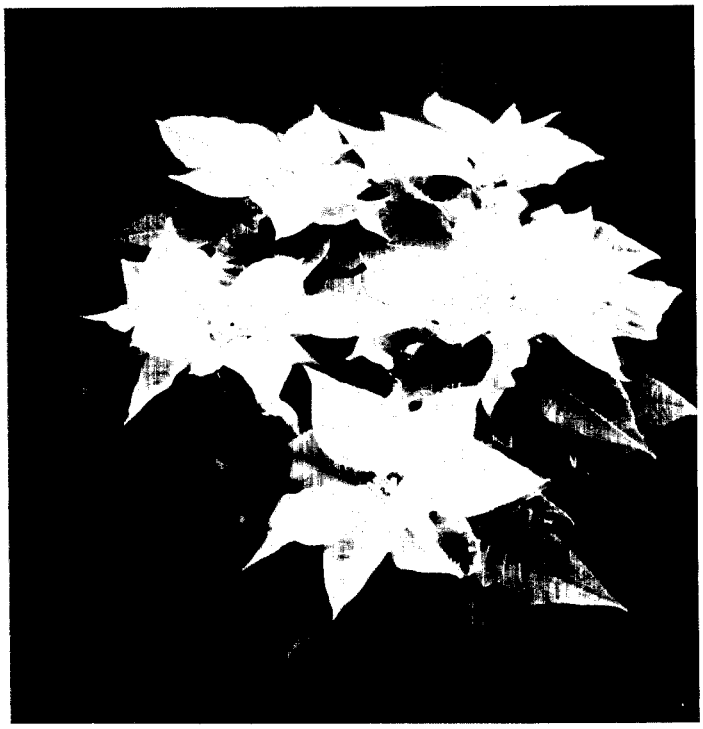

* * * * *